US007258732B2

(12) United States Patent
Nichols

(10) Patent No.: US 7,258,732 B2
(45) Date of Patent: Aug. 21, 2007

(54) STABILIZED SLURRY COMPOSITION AND METHOD OF MAKING THE SAME

(75) Inventor: Carl W. Nichols, Bozeman, MT (US)

(73) Assignee: Luzenac America, Inc., Greenwood Village, CO (US)

( * ) Notice: Subject to any disclaimer, the term of this patent is extended or adjusted under 35 U.S.C. 154(b) by 386 days.

(21) Appl. No.: 10/931,280

(22) Filed: Aug. 30, 2004

(65) Prior Publication Data

US 2005/0081753 A1   Apr. 21, 2005

Related U.S. Application Data

(60) Provisional application No. 60/499,055, filed on Aug. 29, 2003.

(51) Int. Cl.
  *C09C 1/02* (2006.01)
(52) U.S. Cl. ........................... 106/469; 106/486
(58) Field of Classification Search ........ 106/486, 106/469; 501/147, 145
  See application file for complete search history.

(56) References Cited

U.S. PATENT DOCUMENTS

| | | | |
|---|---|---|---|
| 3,586,478 A * | 6/1971 | Neumann | 423/331 |
| 4,118,246 A | 10/1978 | Horzepa et al. | 106/484 |
| 4,144,083 A * | 3/1979 | Abercrombie, Jr. | 501/146 |
| 4,186,027 A | 1/1980 | Bell et al. | 106/486 |
| 4,267,065 A | 5/1981 | Johnson, Jr. et al. | 252/62.62 |
| 4,309,222 A | 1/1982 | Hoyt, IV | 106/487 |
| 4,374,203 A | 2/1983 | Thompson et al. | 501/148 |
| 4,650,521 A | 3/1987 | Koppelman et al. | 524/447 |
| 4,780,147 A | 10/1988 | Ou et al. | 106/415 |
| 5,342,630 A | 8/1994 | Jones | |

(Continued)

FOREIGN PATENT DOCUMENTS

WO   PCT/US04/28384   8/2004

OTHER PUBLICATIONS

U.S. Appl. No. 10/929,344 Hunter et al.

(Continued)

*Primary Examiner*—Jerry Lorengo
*Assistant Examiner*—Pegah Parvini

(57) ABSTRACT

The present invention provides a high solids mineral slurry having long term stability and a method for producing the same. Specifically, the present invention provides a talc slurry having a solids content of up to 65% and a stability against sedimentation for up to 100 days. The talc slurry of the present invention comprises a phyllosilicate mineral, a chelating agent and multivalent ions, wherein the slurry has a pH of between about 10.2 and about 11.8.

38 Claims, 3 Drawing Sheets

U.S. PATENT DOCUMENTS

| | | | | |
|---|---|---|---|---|
| 5,424,259 | A | 6/1995 | Yordan et al. | 501/146 |
| 5,543,372 | A * | 8/1996 | Shi et al. | 501/145 |
| 5,707,912 | A | 1/1998 | Lowe et al. | 501/147 |
| 5,908,708 | A | 6/1999 | Sekutowski et al. | 428/541 |
| 6,027,740 | A | 2/2000 | Puterka et al. | 424/405 |
| 6,069,112 | A | 5/2000 | Glenn et al. | 504/119 |
| 6,074,473 | A * | 6/2000 | Nichols et al. | 106/469 |
| 6,136,740 | A | 10/2000 | Jones et al. | 501/144 |
| 6,156,327 | A | 12/2000 | Sekutowski et al. | 424/405 |
| 6,284,099 | B1 | 9/2001 | Peutherer et al. | 162/158 |
| 6,309,440 | B1 | 10/2001 | Yamashita | |
| 6,555,633 | B1 * | 4/2003 | Tanaka et al. | 526/160 |
| 6,877,275 | B2 | 4/2005 | Glenn et al. | |
| 2003/0159349 | A1 | 8/2003 | Glenn et al. | |

OTHER PUBLICATIONS

Abou-Khaled et al.; 1970; "Effects of Kaolinite as a Reflective Antitranspirant on Leaf Temperature, Transpiration, Photosynthesis, and Water-Use Efficiency"; *Water Resources Res.* 6:280-289.

Adegoroye et al.; 1983; "Initiation and Control of Sunscald Injury of Tomato Fruit Lycopersicon Esculentum, Solar Injury, Radiation Stress"; *J. Am. Soc. Hortic. Sci.*; 108:23-28.

Applications Support Glossary; *The PQ Corporation*; as early as Jun. 17, 2003; pp. 1-20; http:///www.pqcorp.com/technicalservice/glossary.asp.

Arndt; 1992; "Apple Shading to Reduce Heat Damage"; *Tree Fruit Leader VI, Govt of British Columbia, Ministry of Agriculture, Food and Fisheries*; http://www.agf.gov.bc.ca/treefrt/newslett/appleshading.htm.

Basnizki et al.; 1975; The Influence of a Reflectant on Leaf Temperature and Development of the Globe Artichoke (Cynara Scholymus L.); *J. Amer. Soc. Hort. Sci.*; 100:109-112.

Chemical Abstract Service, p. 221.

Drake et al.; 1991; "Quality and Storage of Granny Smith and Greenspur" Apples on Seedlings, M. 26 and MM. 111 Rootstocks; *J. Am. Soc. Hortic. Sci.*; 116:261-264.

Glenn et al.; 2002; "A Reflective, Processed-Kaolin Particle Film Affects fruit Temperature, Radiation Reflection and Solar Injury in Apple"; *J. Am. Hortic. Sci.*; 127:188-193.

Glenn et al.; 1999; "Hydrophobic Particle Films: A New Paradigm for Suppression of Arthropod Pests and Plant Disease"; *J. Econ. Entom.*; 92:759-771.

Glenn et al.; 2001; "Particle Film Application Influences Apple Leaf Physiology, Fruit Yield, and Fruit Quantity"; *J. Am. Soc. Hort. Sci.*; 126:175-181.

"Guar Gum"; as early as Jun. 17, 2003; pp. 1-2; http://www.sbu.ac.uk/water/hygua.html.

Harper et al.; "Cleaning Compounds: Characteristics and Functions"; *Department of Food Science and Technology, Ohio State University*; as early as Jun. 17, 2003; pp. 1-11; http://216.239,51.100/search?q=cache:d9pZuBLHWJAJ:class.fst.ohio-state.edu/fst401/infor . . . .

Khemira et al.; 1993; "Hedgerow Orientation Affects Canopy Exposure, Flowering, and Fruiting of 'Anjou' Pear Trees"; *HortScience*; 28:984-987.

Knight et al.; 2001; "Impacts of seasonal Kaolin Particle Films on Apple Pest Management"; *Can. Entomol.*; 133:413-428.

Liang et al.; 2002; "Repellency of a Kaolin Particle Film, Surround, and a Mineral Oil, Sunspray Oil, to Silverlead Whitefly (*Homoptera:Aleyrodidae*) on Melon in the Laboratory"; *J. Econ. Entomol.*; 95:317-324.

Lipton; 1977; "Ultraviolet Radiation as a Factor in Solar Injury and Vein Tract Browning of Cantaloupes"; *J. Am. Soc. Hortic. Sci.*; 102:32-36.

"Locust Bean Gum"; as early as Jun. 17, 2003; pp. 1-2; http://www.sbu.ac.uk/water/hyloc.html.

Mitchum; "Fruit Physiological Disorders: Apple Sunburn Sunscald"; *Postharvest Technology Research and Information Center, University of California at Davis*; 1996-2004; pp. 1-2; http://postharvest.ucdavis.edu/produce/disorders/apple/pdapsun.shtml.

Parchomchuk et al.; 1996; "Orchard Cooling With Pulsed Overtree Irrigation to Prevent Solar Injury and Improve Fruit Quality of 'Jonagold' Apples"; *HortScience*; 31:802-804.

Puterka et al.; 2000; "Progress Toward Liquid Formulations of Particle Films for Insect and Disease Control in Pear"; *Environ. Entomol*; 29:329-339.

Roberts et al.; 1994; "Canopy Shade and Soil Mulch Affect Yield and Solar Injury of Bell Pepper"; *HortScience*; 29:258-260.

Schrader et al.; "Raynox for Suppression of Pests in Apple and Pear"; *Washington State University Cooperative Extension Service*; (date unknown); http://www.tfrec.wsu.edu/staff/les.htm; 1 p.

Schrader et al.; "Stress-Induced Disorders: Effects on Apple Fruit Quality"; *Washington Tree Fruit Postharvest Conference*; Dec. 2-3, 2003; pp. 1-7.

Schupp et al.; 2002; "Effect of Particle Film on Fruit Sunburn, Maturity and Quality of 'Fuji' and 'Honeycrisp' Apples"; *Hort. Technology*; 12:87-90.

"Slip Information from Dalzell Crafts and Ceramics, Your Source for Bisque"; *DCC*; as early as Jun. 17, 2003; pp. 1-2; http://216.239.51.100/search?q=cache:2xomX3xEnvUJ:www.dalzell.net/ceramics/slip.html+ . . . .

Sparks; 1995; "Environmental Soil Chemistry: Chapter 2: Inorganic Soil Components"; *Academic Press*, San Diego; p. 36.

Spayd et al.; "Separation of Sunlight and Temperature Effects on the Composition of *Vitis vinifera* cv. Merlot Berries"; *Am. J. Enol. Vitic.*; 2002, 53:3; pp. 171-182.

Stemmermann et al.; 1978; "Talc-Coated Rice as a Risk Factor for Stomach Cancer"; *Am. J. Clin. Nutr.*; 31:2017-2019.

Stem: "Particle Film Enters the Picture: Whitewash-like Spray Repels Pome Fruit Pests, Helping Cut Pest-Control Costs"; *The Grower*;date unknown; pp. 1-3; http://www.growermagazine.com/home/04-02surround.html.

"Surround Crop Protectant"; *Surround WP Manufacturer*; Engelhard Corporation, 101 Wood Avenue, P.O. Box 770, Iselin, NJ 08830-0770; 2pp.; http://www.surround.engelhard.com.

"Surround Wp Crop Protectant—Specimen Label"; Engelhard; as early as Mar. 26, 2001; 9pp.

"Talc Mineral Data Pronunciation Guide"; *Trinity Mineral Co.—Rare Minerals*; Apr. 20, 2003; pp. 1-3; http://webmineral.com/data/Talc.shtml.

"Understanding Plainsman Data Sheets"; *Plainsman Clays Ltd.*; as early as Jun. 10, 2003; pp.1-6; http://digital fire.com/plainsman/overview.shtml.

Unruh et al.; 2000; "Particle Films for Suppression of the Codling Moth (*Lepidoptera:Torticidae*) in Apple and Pear Orchards"; *J. Econ. Entomol.*; 93:737-743.

"Virta; United Staes Geological Survey"; 2002; Minerals Yearbook.

Warmund; "Top Crops"; *University of Missouri, in cooperation with the Missouri State Horticulture Society*; Summer 2004; pp. 1-6; http://www.agebb.missouri.edu/hort/topcrops.htm.

\* cited by examiner

STABILIZED SLURRY COMPOSITION AND METHOD OF MAKING THE SAME

CROSS REFERENCE TO RELATED APPLICATIONS

This application claims priority to U.S. Provisional Patent Application Ser. No. 60/499,055, filed Aug. 29, 2003, which is incorporated herein in its entirety by this reference.

FIELD OF THE INVENTION

The invention resides in the field of phyllosilicate slurries having increased stability to sedimentation.

BACKGROUND OF THE INVENTION

Phyllosilicate minerals such as kaolinite, talc, chlorite, pyrophyllites and montmorillonite are minerals which contain basic silicates and are used in a variety of applications such as paper manufacturing, talcum powder, tailor's chalk, cosmetics and lubricants. With regards to talc, a slurry of talc is commonly used in paper manufacturing to control, inter alia, pitch and paper coating. To manufacture these slurries, talc is added to water until a suspension having a desired solids content is produced. This process is conventionally referred to as a "makedown" process. Currently available makedown processes yield a talc slurry having about 25-60% solids with a reasonable viscosity.

A large quantity of talc is used in the paper and other industries and reducing the transportation costs of these materials to the customer is the subject of considerable effort. High solids slurries of talc are desirable because they increase the transportation cost effectiveness. However, settling occurs when these higher concentration talc slurries are permitted to stand without agitation as often takes place during shipping and in storage. This results in a thick viscous mass or gel after several days and a dense flocculate at the bottom of the shipping container after longer storage, requiring the customer to employ mechanical devices and considerable effort to redisperse the slurries or to add various chemicals to render the slurries usable. Often, the slurries are returned to the manufacturer as unacceptable.

To overcome these problems, manufacturers and suppliers of phyllosilicate minerals have employed different means of making and shipping mineral slurries to customers. Methods such as shipping in low concentrations, mixing higher concentration slurries with various chemical dispersants, shipping solid ground mineral to regional distribution centers where the slurry is prepared and shipped to nearby customers are all currently employed to deliver a useable mineral slurry product to customers without settling of the product.

U.S. Pat. No. 5,424,259, issued to Yordan et al., discloses a method of making a kaolin clay slurry having at least 50% by weight of kaolin clay by mixing water and a lithium based dispersant and then mixing structured kaolin clay particles with the aqueous composition to form the desired high solids slurry.

U.S. Pat. No. 4,118,246, issued to Horzepa et al., discloses a process for producing kaolin clay slurry having 60% to 70% by weight of kaolin clay using a dispersant and a micromixer. This process requires a use of the special micromixer apparatus.

U.S. Pat. No. 4,144,083, issued to Abercrombie, Jr., provides a method for maintaining the low shear viscosity of a kaolin clay slurry having 60% to 72% by weight of kaolin clay using 0.5 to 3.0 pounds of citric acid or sodium citrate per ton of kaolin clay.

U.S. Pat. No. 4,186,027, issued to Bell et al., discloses a process for making kaolin slurry at a pH from 7.5 to 10.5, having a solids content in the range of from 60% to 75% by weight using a dispersing agent and a water-soluble organic polymer. The slurry is subjected to a particle size separation to reduce the percentage of the particles larger than 10 μm in the slurry to not more than 3% by weight.

U.S. Pat. No. 4,309,222, issued to Hoyt, IV, provides a method for making a kaolin slurry of reduced low shear viscosity in water at a pH of 6 to 8 having a solids content from about 60% to 72% using citrate and polyacrylate.

U.S. Pat. No. 4,650,521, issued to Koppelman et al., provides a process for making a kaolin slurry having a solids content of at least about 65% using a carbonate, a water-soluble organic polyacrylate and a water-soluble anionic phosphate. The slurry is then subjected to a "degritting" process to reduce the percentage of the particles larger than 45 μm in the slurry to not more than 0.2% by weight.

U.S. Pat. No. 4,374,203, issued to Thompson et al., provides a method for making a clay slurry having at least 50% by weight of the clay using anionic and cationic polymers.

In U.S. Pat. No. 6,074,473, issued to Nichols et al., provides a method of using pH adjustment and inorganic salts to disperse talc in a slurry.

However, for various reasons such as limited stability, a need for the use of organic polymers, special mixers and/or a need for particle size separation, the prior art fails to provide an acceptable process for producing low cost, high solids phyllosilicate mineral slurry having desired rheological properties that is sufficiently stable for lengthy storage or long distance transport. Therefore, there is a need for an inexpensive and effective method of preparing a stable phyllosilicate slurry having high solids content.

SUMMARY OF THE INVENTION

The present invention is directed to a phyllosilicate mineral slurry containing a phyllosilicate mineral, a chelating agent and at least one multivalent ion, in slurry with a pH of between about 10.2 and about 11.8. The phyllosilicate mineral may be kaolinites, talc, chlorites, pyrophyllites, montmorillonites, smectites and/or vermiculites. Preferably, the phyllosilicate mineral is talc. The phyllosilicate mineral typically represents between about 50% and about 80% of the slurry by weight. Preferably, the phyllosilicate mineral represents at least about 60% of the slurry by weight. Additionally, the phyllosilicate mineral slurry also contains sodium hydroxide.

The chelating agent may be sodium polyacrylate, sodium maleate, citric acid, sodium citrate, sodium silicate, EDTA, DTPA or mixtures thereof. Preferably, the chelating agent is citric acid in a concentration range of between about 50 ppm and about 850 ppm citric acid. More preferably, the slurry contains between about 400 ppm and about 700 ppm citric acid.

The multivalent ions may be cations including, but not limited to, magnesium ions and/or aluminum ions. Additionally or alternatively, the multivalent ions may be anions such as sulfate ions and/or citrate ions. Preferably, the multivalent ions are added to the slurry in the form of Epsom salt (magnesium sulfate heptahydrate) and/or alum (aluminum sulfate). Magnesium sulfate heptahydrate may be added to the slurry in the amount of between about 100 ppm to about 1500 ppm. Preferably, magnesium sulfate heptahydrate is added to the slurry in the amount of between about 700 ppm to about 1300 ppm.

Where the sequestering agent used is citric acid and the multivalent ions used are magnesium and sulfate ions from Epson salt, the Epson salt is preferably used in a stoichiometric amount greater than the stoichiometric amount of citric acid.

The pH of the slurry is preferably between about 10.2 and about 11.8 and the slurry has a specific gravity of between about 1.5 and about 1.8, has a viscosity of less than about 500 centipoise after agitation, at least about 40,000 centipoise after storage for greater than about 4 hours after formulation, a mass median $d_{50}$ of from about 1.2 µm to about 3.5 µm, and is stable for at least about 25 days and typically much longer.

In another embodiment of the invention, a method of making a stable phyllosilicate mineral slurry is provided. The method includes adding a phyllosilicate mineral to a solvent to produce a substantially homogeneous high solids slurry. A chelating agent is added to the slurry and one or more multivalent ions are added to the slurry to produce a stable phyllosilicate mineral slurry. The pH of the slurry may be adjusted to between about 10.2 and about 11.8.

The phyllosilicate mineral used in the method may be kaolinites, talc, chlorites, pyrophyllites, montmorillonites, smectites and/or vermiculites. Preferably, the phyllosilicate mineral is talc. The phyllosilicate mineral typically represents between about 50% and about 80% of the slurry by weight. The chelating agent added to the slurry may be sodium polyacrylate, sodium maleate, citric acid, sodium citrate, sodium silicate, EDTA, DTPA and mixtures of these chemicals. The multivalent ions may be cations such as magnesium ions and/or aluminum ions, or anions such as sulfate ions and/or citrate ions. The multivalent ions may be added to the slurry in the form of Epsom salts (magnesium sulfate heptahydrate) in an amount of between about 100 ppm to about 1500 ppm.

DETAILED DESCRIPTION OF THE INVENTION

Figure 1:
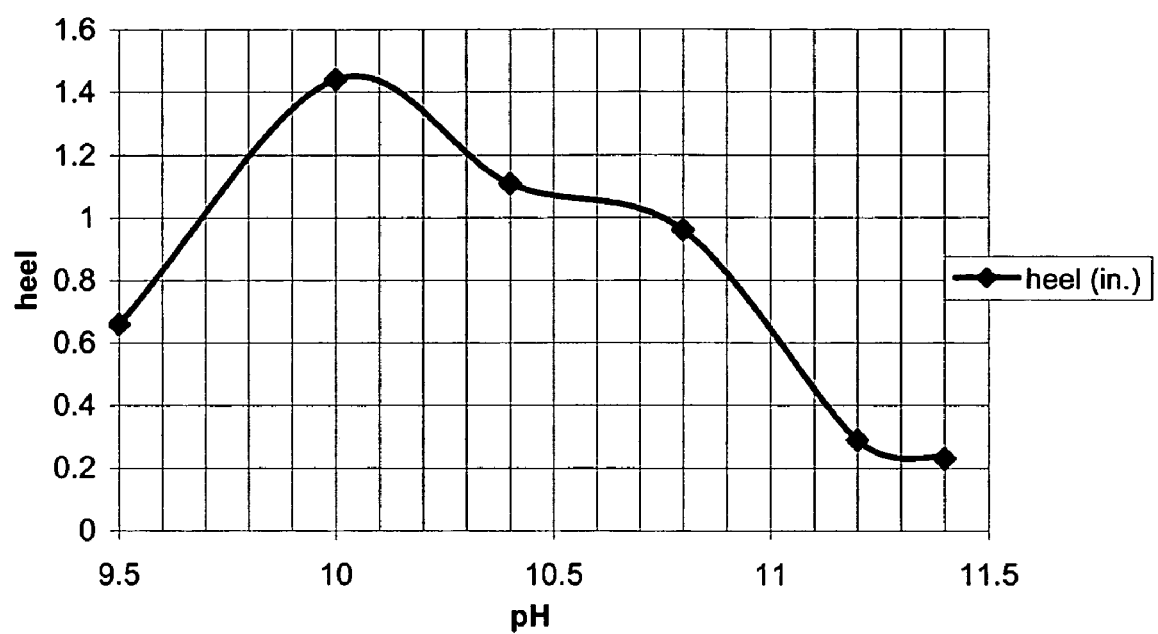
FIG. 1 shows a pH stability study conducted on a talc slurry of the present invention containing 200 ppm Epsom salt and 700 ppm citric acid.

The present invention provides means of forming mineral slurries that are highly stable during transport and storage. Using chelating agents, multivalent ions and pH control, the present invention provides a mineral slurry that is stabilized to prevent sedimentation for at least about fifty days and often much longer.

As used in the present disclosure, the term "stability" specifically means that the individual mineral particles in the slurry of the present invention refrain from coagulation or flocculation in suspension or coalescence on the bottom of the container. Stability comes from having a very uniform electrostatic charged field around each particle in the suspension. The electrostatic particle-to-particle repulsion will exceed gravity forces that seek to drive sedimentation of the suspension. For practical purposes of the present disclosure, a suspension is considered to be stable if the coagulation process is so slow as to take at least about fifty days to form a noticeable precipitate in an undisturbed shipping container.

The term "phyllosilicate mineral" (phyllosilicate) refers to those minerals that contain basic silicates. Preferably the phyllosilicate is selected from the group consisting of kaolinites, talcs, chlorites, pyrophyllites, montmorillonites, smectites and vermiculites. More preferably, the phyllosilicate is selected from the group consisting of talcs and pyrophyllites, and most preferably the phyllosilicate is talc. "Improved rheological properties" and "a low viscosity" means that the flow characteristics of the slurry of the present invention are improved over the flow characteristics of a conventional talc slurry when the two slurries are compared at equivalent solids content and that the slurry of the present invention can be worked and/or pumped by means which are conventional in the talc industry, depending on the desired use of the slurry. The slurry of the present invention has a rheology which permits, among other things, ease of transfer and use. Preferably the viscosity of the slurry is less than about 500 centipoise (cps), more preferably less than about 350 cps, and most preferably less than about 200 cps.

The term "high solids" refers to those slurries in which the content of phyllosilicate mineral is at least about 50% by weight, preferably at least about 60% by weight and more preferably at least about 64% by weight. The phyllosilicate mineral content can be as high as is practical for acceptable viscosities during handling and transport. For example, the phyllosilicate mineral content can be less than about 80% by weight. As used in this invention, parts per million (ppm) values are reported on by weight of dry solids basis, i.e., not including water or any other solvent, unless noted otherwise.

The Schulze-Hardy rule for flocculation of liquid colloidal dispersions (also known as sols) holds that the flocculating value of an electrolyte is predominantly determined by its valence rather than its type. Consequently, divalent and trivalent cations or anions are significantly more powerful in flocculating a sol than monovalent ions in solution. The stabilizing technology of the present invention uses multivalent cations and anions as antagonists to the dispersing action of special chelating or dispersing agents. The best rheology of the final slurries of the present invention is obtained by following specific process steps, but the stabilizing results are not dependent on these steps.

The multivalent ions of the present composition can be provided by salts that possess both multivalent cations such as magnesium (+2) and aluminum (+3) and multivalent anions such as sulfate (−2). More particularly, multivalent cations useful in the present invention include magnesium (+2) and aluminum (+3). Multivalent anions useful in the present invention include sulfate (−2), citrate (−3), phosphate (−4), silicate (−2) and borate (−2). In a preferred embodiment, multivalent ions are supplied by addition of magnesium sulfate heptahydrate (Epsom salt) or aluminum sulfate double salts (alum) to a phyllosilicate mineral slurry, preferably in an amount between about 100 ppm and about 1500 ppm, more preferably between about 700 ppm and about 1300 ppm, and more preferably at about 700 ppm.

The chelating agents of the present invention are molecules with monovalent anionic sites on a multivalent backbone. Whereas dispersants will adsorb on a mineral surface without reacting to it, chelating agents chemically attack and bind to multivalent cations of metals like magnesium, iron, aluminum, calcium and barium. Thus, chelating agents added to the talc in the present invention bind to active metal cation sites on the talc (i.e. magnesium in the brucite). The chelating agent also tries to bind with magnesium in solution. The preferred chelating agents are sodium acrylate, sodium maleate, citric acid, sodium citrate, sodium silicate, EDTA, DTPA and combinations of these agents. Most preferably, the chelating agent is citric acid. When the chelating agent is citric acid, it is typically present in the slurry in a concentration of between about 50 ppm to about 850 ppm and more preferably at between about 400 ppm and about 700 ppm. The multivalent cations react with chelating agents which function as polymeric molecules with multiple anionic sites. This reaction may proceed slowly due to the need of the multivalent cation to capture several anionic sites to reach electrostatic neutrality. Thus, the chelating agent operates by wrapping around a multivalent cation, which is attached to the phyllosilicate particle, thereby keeping the phyllosilicate particle in suspension.

Therefore, one embodiment of the present invention is a process of making a high content, stable mineral (e.g., talc) slurry by attaching a multivalent chelating agent onto the edge of the mineral. This is possible by first adding the chelating agent to the suspension in which the talc particle is dispersed in a high pH aqueous environment. The crystal structure of talc is such that there is a net negative electrostatic charge on the faces and a net positive charge on the edges of the crystal. The chelating agent attaches to the edges of the talc, as there are magnesium cations in the crystal lattice as brucite. The chelating agents cannot remove the magnesium, and therefore become electrostatically bound to the talc. After addition, the chelating agent may be allowed to disperse before addition of the multivalent ions to allow for interaction between the chelating agent and the phyllosilicate material. However, the attachment rates are very rapid in a dispersed slurry such that the chelating agent and magnesium can be combined in the same solution before adding them together to the slurry. No reaction takes place between the chelating agent and the magnesium prior to their addition to the slurry due to the acidic environment. Upon introduction to the slurry, the chelating agent immediately attaches to talc before the magnesium balances the chemistry.

The pH of the slurry ranges from about pH 10.2 to about pH 11.8, more preferably from about pH 10.8 to about pH 11.5, and most preferably is about pH 11.3. The pH of the slurry can be adjusted after the slurry has formed, continuously throughout the makedown process, during each addition of phyllosilicate mineral, or at any time during the makedown process. Preferably, the pH of the slurry is maintained at a desired level throughout the makedown process. This can be achieved by continuously monitoring the pH of slurry and adjusting the pH as needed. The monitoring and addition of a caustic (e.g., sodium hydroxide) can be done manually or it can be done automatically, e.g., by a computer controlled process.

An excess of multivalent cations such as aluminum or magnesium are then added. The chelating agent attempts to wrap around these cations as well but is unable to as it is already attached to the mineral surface in a linear arrangement. If the pH of the slurry is outside of the range noted above, magnesium or aluminum cations will typically cause a rheology crisis within a mineral slurry manifested by rheopectic behavior. However, without intending to be bound by any one theory, when used in the methodology of the present invention, divalent anions such as sulfate, phosphate and tetraborate, appear to act as anionic dispersants maintaining low viscosity during gentle or severe agitation. The methodology of the preferred embodiments of the present invention do not induce any rheopectic or dilatent behavior in the mineral slurry. Thus, the addition of salts composed of multivalent cations and anions to the mineral slurry containing chelating agents creates an ionic environment leading to a slurry having long-term stability.

The makedown process of the present invention can include adding a feedstream of phyllosilicate to the aqueous composition at a rate and under conditions sufficient to obtain a substantially homogeneous high solids slurry. Preferably, the mass median $d_{50}$ of the phyllosilicate is less than about 7 microns (μm), more preferably from about 1.2 μm to about 3.5 μm. A "mass median $d_{50}$" refers to a particle size distribution wherein about 50% of total weight of phyllosilicate is due to particles having less than the mass median $d_{50}$ particle size. Alternatively, it is preferred that the particle size of about 100% of phyllosilicate particles is less than about 65 μm, more preferably less than about 55 μm and more preferably less than about 45 μm in the longest dimension.

Alternatively, instead of comminuting the phyllosilicate mineral to a desired particle size prior to the makedown process, a high solids content slurry makedown process of the present invention can be conducted prior to a comminuting process. For example, a high solids content slurry having a relatively large phyllosilicate particle size can be subjected to a wet-milling process to produce a slurry having a desired phyllosilicate particle size. In this manner, the milling process also provides the shearing action required for the makedown process. Moreover, this wet-milling eliminates a need for a separate entrained air removal step, as described below.

The ease of preparation of a high solids content low viscosity slurry can be dependent on the temperature of the slurry during the makedown process. Preferably, the temperature of the slurry is maintained at from about 32° C. to about 90° C. during the makedown process, more preferably from about 34° C. to about 60° C., and most preferably at least about 46° C. It should be appreciated that the above temperature refers to a temperature during a makedown process only; thus, after the makedown process, the temperature of slurry can be lowered to less than 32° C.

The makedown process can be facilitated by high shear agitation of the aqueous composition as the feedstream of phyllosilicate is added to a mixing tank. Preferably, the tip speed of the mixer blade in the mixing tank is from about 4000 feet per minute (fpm) to about 9000 fpm.

The presence of air in the slurry affects the viscosity of the slurry. It is believed that the primary source of air is from the agglomerated phyllosilicate particles. The agglomerated phyllosilicate particles can be 40% air with phyllosilicate particles being held together by van der Waals forces. During the makedown process, air is released from the phyllosilicate particle surface in the slurry but is held in the slurry suspension. Preferably the slurry contains less than about 3.5% by volume of entrained air, more preferably less than about 2%, and most preferably less than about 1%.

One can reduce the amount of entrained air in the slurry by allowing the air to escape from the slurry during the makedown process. This provides a slurry with a reduced viscosity. The removal of entrained air can be accomplished by stopping the high shear agitation for a time sufficient to allow the entrained air to escape or by transferring the slurry to a holding tank.

The slurry produced by the present invention will typically have a specific gravity of between about 1.60 and about 1.73, more preferably between about 1.62 and about 1.70, and even more preferably between about 1.64 and about 1.68.

An apparatus having at least a two tank system is preferred in the makedown process. In this apparatus, the first tank (i.e., the mixing tank) provides a high shear agitation and is used for mixing the slurry. The slurry is then transferred to a second tank (i.e., the holding tank) which does not have a high shear agitation. The second tank provides a rest time for the slurry (i.e., no high shear agitation), thus allowing entrained air to escape and to allow equilibration of particle surface with the electrolytes in solution. To facilitate the removal of air and a complete solvation of the surface area of the phyllosilicates, the holding tank is typically agitated for about 10 minutes per hour. In this manner, the viscosity of slurry can be reduced from between about 800 to about 1600 cps to between about 200 cps to about 350 cps. The holding tank can have a conical bottom having at least about a 55° angle to about a 60° angle, preferably at least about a 55° angle, and more preferably about a 60° angle. Optionally, the portion of the slurry which is in the bottom of the holding tank is transferred to the first tank (i.e., mixing tank) to continue its mixing. Typically the holding tank is much larger than the mixing tank to allow the slurry to rest for a sufficient time to allow at least part of the entrained air to escape from the slurry. In some instances, the escaping air causes formation of a foam in the holding tank. If this occurs, the amount of foam in the holding tank can be reduced by spraying the foam with a dilute dispersant. Preferably the dispersant comprises the same salt and/or caustic as that used for the makedown process.

The slurries of the present invention have the normal pseudoplastic rheology in an agitated state that is expected from such mineral slurries. This behavior is consistent over a wide range of temperature from freezing to temperatures as high as 150° F. and above. On standing for as little as about four hours, the slurry can develop a gelled characteristic. The fluid form is described as a "Bingham plastic." A degree of fluid shear must be imparted to start the fluid moving again. Viscometer tests indicate low speed viscosities of at least about 40,000 cps on a standing gel that breaks down to less than about 500 cps once flowing. This reversible plastic behavior in conjunction with the electrostatic sol stabilization is thought to be the cause for the exceptional functional slurry stability of the slurries of the present invention.

The stoichiometry of the reaction guides the formation of the optimal stabilizing formulation. For example:

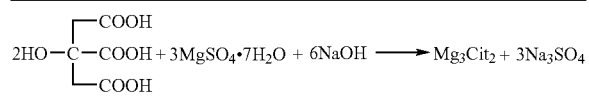

| Citric acid | Epsom salt | Base | Magnesium Citrate | Sodium Sulfate |
|---|---|---|---|---|
| MW = 192.2 | 246.3 | 40.6 | | |
| 384 | 738 | 240 | | |
| 200 ppm | 384 ppm (stoichiometric ratio of salt and chelating agent) | | | |
| or 400 ppm | and 768 ppm | | | |

It has been discovered empirically that significant reductions in the amounts of citric acid or EDTA generate better stability than precise stoichiometric ratios of these two chelating agents in certain specific talcs. For example, talcs acquired from sources originating in Montana were best stabilized at stoichiometric levels of citric acid and Epsom salt (i.e. about 700 ppm citric acid and 1300 ppm Epsom salt). Alternatively, talc derived from Canadian sources was found empirically to be best stabilized at non-stoichiometric levels of citric acid and Epsom salt representing a decrease in citric acid under stoichiometric levels of about six-fold (i.e. about 100 ppm citric acid and 1200 ppm Epsom salt).

Although many different solvents can be used in making slurries of the present invention, the preferred solvent is water. Upon the introduction to hard water, chelating agents encounter metal cations ($Mg^{++}$ and $Ca^{++}$). The quantities of the chelating agents used in these mineral slurries are lower than stoichiometric amounts given the content of divalent cations in the hard water. For this reason, the methods of producing the mineral slurries of the present invention include the makedown at elevated pH before the chelating agent is introduced. The elevated pH causes precipitation of cations found in hard water. The chelating agents then have a much higher probability of attachment to the cationic sites at the edge of the mineral rather than sequestering minerals in hard water. Thus, the dispersion of the slurry or "makedown," is completed before the chelating agents and salts are added to assure proper attachment to the edge of the mineral for stabilization of the mineral slurry.

The presence of carbonate minerals in talc products such as dolomite or magnesite will influence the ratio of stabilizing chemicals. Examinations conducted to test for reduced sedimentation rates in slurries of the present invention formed with talc from different sources and citric acid and Epsom salt resulted in the selected ratios shown in Table 1.

TABLE 1

| Talc source | Production Process | Citric acid | Epsom salt | Level of Epsom salt above stoichiometric amount of citric acid used |
|---|---|---|---|---|
| Penhorwood, Ontario | Dry grind | 200 PPM | 700 PPM | 1.8 × Epsom |
| Penhorwood, Ontario | Reduced surface energy | 100 PPM | 1200 PPM | 6.25 × Epsom |
| Yellowstone, Montana | Reduced surface energy | 700 PPM | 1300 PPM | 0.97 × Epsom |

These ratios selected in Table 1 are not necessarily at the limits of the best performance but are instead selections of levels that provide a functional stability. In various embodiments, the ratio of citric acid to Epsom salt ranges from about 1:1 to about 1:20. Although, the selection process shows increasing stability with higher concentrations of salts, the best balance for different mineral slurries is often based not only on stability but on a combination of stability, cost and rheology considerations.

Talc products used for pitch control contain some impurities that prevent complete suspension stability. However, using the slurries with electrostatic uniformity and sufficient solids content prepared using the methods and chemistry of the present invention, it is possible to form a slurry having a stability that allows for successful transport and unloading of containers of slurry that have been in transit and storage for as long as about 25 days, about 50 days, about 75 days, about 100 days, or about 200 days.

EXAMPLES

Example 1

This example describes experiments conducted to discover an optimum ratio and concentration of stabilizing chemicals for a high pH talc slurry. The test slurries were placed into 400 cc jars and various ratios of acid and salt added into each jar. Sedimentation heels were measured by weighing the portion of product that would not pour out of the jar. Sedimentation was greatly accelerated by the small jars and mixing process. It has been assumed that the comparison of small jar tests is related to larger containers.

A linear test of the concentrations of citric acid to Epsom salt was conducted with the ratios shown in Table 2.

TABLE 2

| Sample | Citric acid | Epsom salt | Hot viscosity 60° C. | Cold viscosity 30° C. | Heel-grams |
|---|---|---|---|---|---|
| 1 | 100 | 800 | 175 | 283 | 235 |
| 2 | 250 | 750 | 175 | 284 | 225 |
| 3 | 400 | 600 | 178 | 280 | 415 |

Tests indicated a 2:1 ratio of Epsom to citric. Some tests, not reported in Table 2, show that a higher ratio of about 2.6:1 to about 5:1 is better. These results suggest that concentrations of 200 ppm citric acid and 700 ppm Epsom salt are preferred. Sodium sulfate was also found to be useful in stabilizing slurry at a ratio of 3.5:1.

Example 2

This Example shows the results of studies performed to evaluate a range of pH values, citric acid concentrations and Epsom salt concentrations on talc slurry viscosity and precipitate (heel) formed.

The pH range was initially tested by preparing a stock slurry at pH 9.5. Individual 400 ml samples of this stock slurry were taken and set to higher pH values. The observations of viscosity and sedimentation both indicate a range of useful pH with the best pH being 11.5 as shown in FIG. 1.

Figure 2:
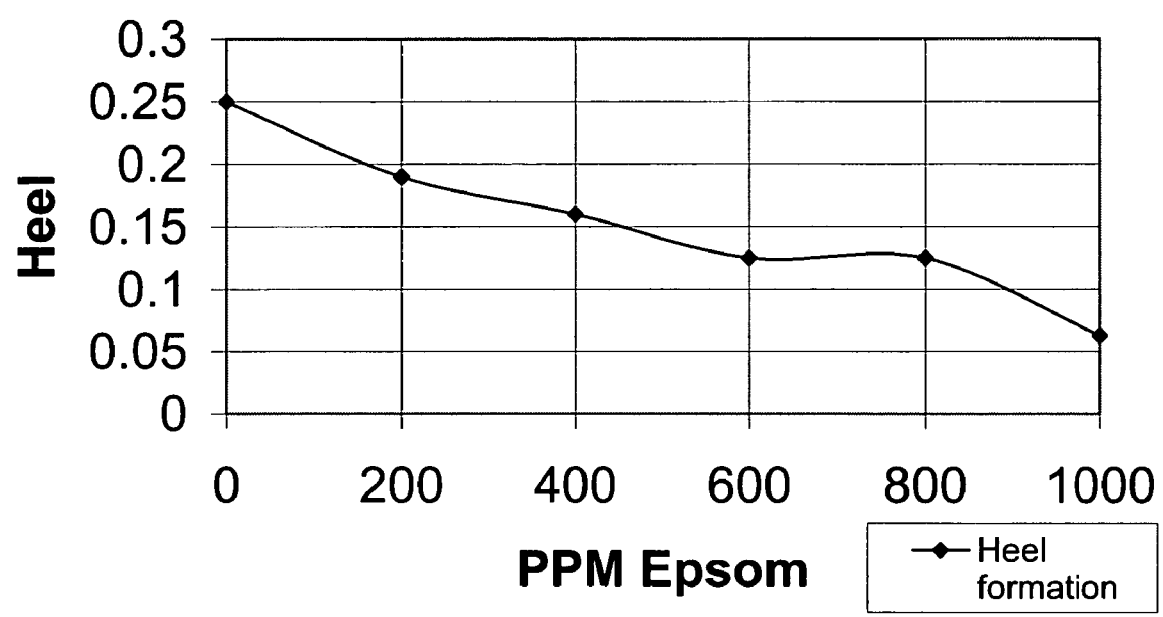
FIG. 2 shows a stability study conducted on a talc slurries of the present invention containing different amounts of Epsom salt in slurries having 200 ppm citric acid and pH of 11.3.

Two additional series of tests were conducted to test the levels of Epsom salt and citric acid. The first set was made down with 200 ppm citric acid and individual samples taken and set to Epsom salt levels from 0 to 1000 ppm. The results shown in FIG. 2 are not significantly different when pH is constant. The better stability is at the higher test concentration of 1000 ppm Epsom salt.

Figure 3:
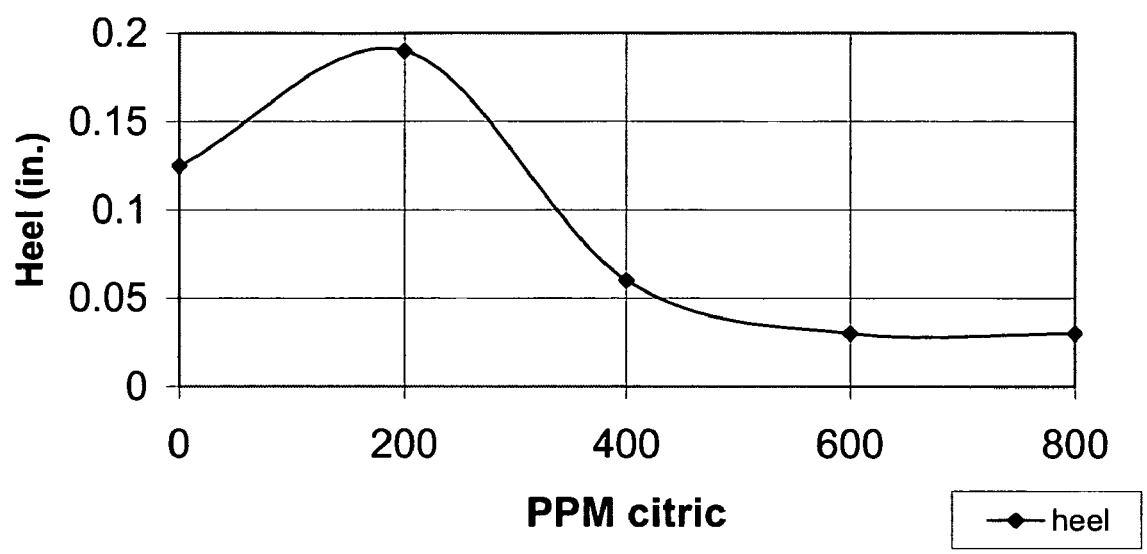
FIG. 3 shows a stability study conducted on a talc slurries of the present invention containing different amounts of citric acid with Epsom salt concentration set at 800 ppm.

In the second series of tests, Epsom salt was set at 800 ppm and citric acid concentrations were varied on each sample. In the slurry preparation, citric acid was added and dispersed first before Epsom salt was added. The results of this series is shown in FIG. 3. The typical response seen with talc was higher citric acid levels increasing heel formation. These results suggest that citric acid should be from 400 to 800 ppm and the Epsom salt should be from 800 to 1000 ppm with pH set at about 11.2 to 11.5 with a broader range being acceptable for each of these values.

Example 3

This example presents a formulation study of the effect of pH on a talc slurry formed with citric acid and Epsom salt additives.

The talc slurries were prepared at different pH with the formulation shown in Table 3.

TABLE 3

| Ingredient | Concentration (wt. %) |
|---|---|
| Talc | 63 |
| Water | 37 |
| K Flow | 0.4 |
| Dowfax | 0.9 |
| NaOH | 0.033 |
| Citric acid | 0.01 |
| Epsom Salt | 0.12 |
| Busan 1202 | 0.005 |

To this formulation, different amounts of NaOH were added to produce slurries of progressively higher pH. The effect of pH on the formulation characteristics and precipitate (heel) formation in a 400 cc jar of each slurry are shown in Table 4.

TABLE 4

| Sample | PH at 140° F. | pH at 65° F. | ppm NaOH | Heel (inches) | Slurry character |
|---|---|---|---|---|---|
| 1 | 9.0 | 9.2 | 325 | 3.000 | Hard |
| 2 | 9.5 | 9.4 | 473 | 3.000 | Soft |
| 3 | 10.0 | 9.9 | 670 | 3.000 | Soft |
| 4 | 10.5 | 10.4 | 870 | 3.000 | Soft |
| 5 | 11.0 | 10.9 | 1049 | 0.250 | Rubbery fluid |
| 6 | 11.5 | 11.5 | 1309 | 0.063 | Fluid |

The tests showed that the formula was stable at pH 11.5. The high pH formula can be used to eliminate components which cause biological growth problems. The citric acid and Epsom salts do not react unless the system pH is high. The salts probably do not react at the lower pH levels.

Example 4

This example presents the results of a stability study conducted on a talc slurry stabilized with a combination of citric acid and Epsom salt.

The talc slurry was prepared with the formulation shown in Table 5.

TABLE 5

| Ingredient | Concentration (wt. %) |
|---|---|
| Talc | 64 |
| Water | 35 |
| K Flow | 0.4 |
| Dowfax | 0.9 |
| NaOH | 0.12 |
| Citric acid | 0.02 |
| Epsom Salt | 0.07 |
| Busan 1202 | 0.01 |

The slurry was made down with a Cowles mixer. Slurry solids content was set at 64% and viscosity tested at 120° F. The viscosity was higher than typical 1-gallon KADY mill batches due to low makedown temperature of 120° F. and lower shear of the Cowles mixer. The slurry was drained into a 55-gallon polyethylene drum for observation. Stability observations were made regularly for 81 days and seven time points are described in Table 6.

TABLE 6

| Days | Clear water on top | Slurry character | Heel |
| --- | --- | --- | --- |
| 0 | start at 64% solids | | pH = 11.4 |
| 1 | Slight film | Very thin gel | Thin film of heel on bottom |
| 5 | 1/16" water | Thin gel | 1/4" soft heel |
| 15 | 1/8" water | Soft gel | 1/4" soft heel |
| 36 | 1/4" water | Soft gel | 1/2" inch soft heel. pH = 10.9 No odor observed |
| 48 | 1/2" water | Soft gel | 3/4" soft heel. Slight biological odor is developing. pH 10.8 |
| 81 | 1" water | Soft gel | 1" soft heel. Mild rancid odor. pH 10.8 |

These observations demonstrate the stability of the citric acid and magnesium containing talc slurry up to 81 days of storage without curdling of the slurry gel.

Example 5

This example demonstrates the effect of the addition of alum (aluminum sulfate) on the stability of a talc slurry.

Three talc slurries were prepared having about 63% talc and 37% water. Different combinations of citric acid, Epsom salt and alum were added to the slurries for comparative purposes. The formulations and effects on precipitate (heel) formation are shown in Table 7.

TABLE 7

| Slurry Sample | Citric Acid (wt. %) | Epsom Salt (wt. %) | Alum (wt. %) | Heel (inches) |
| --- | --- | --- | --- | --- |
| 1 (control) | 0 | 0 | 0 | 2.4 |
| 2 | 0.07 | 0.130 | 0 | 0.125 |
| 3 | 0.07 | 0.130 | 0.07 | 0.03 |

These results show that alum added to the stabilized slurry flocculates fines and enhances stability.

What is claimed is:

1. A stable talc slurry, comprising:
water;
between about 50% and about 80% talc by weight;
sodium hydroxide;
between about 50 ppm and about 850 ppm citric acid;
between about 700 ppm and about 1300 ppm magnesium sulfate heptahydrate; wherein the slurry has a pH of between about 10.2 and about 11.8 and the slurry is stable without agitation for at least about 25 days.

2. A method of making a phyllosilicate mineral mineral slurry, comprising:
adding a phyllosilicate mineral to a solvent to produce a substantially homogeneous high solids slurry;
adding citric acid to the slurry; and,
adding multivalent ions to the slurry comprising the chelating agent to produce a stable phyllosilicate mineral slurry.

3. A method of making a phyllosilicate mineral mineral slurry, comprising:
adding a phyllosilicate mineral to a solvent to produce a substantially homogeneous high solids slurry;
adding a chelating agent to the slurry; and,
adding magnesium sulfate heptahydrate to the slurry comprising the chelating agent to produce a stable phyllosilicate mineral slurry.

4. The talc slurry of claim 1, wherein said talc comprises at least about 60% of the slurry by weight.

5. The talc slurry of claim 1, wherein the slurry comprises between about 50 ppm to about 850 ppm citric acid.

6. The talc slurry of claim 1, wherein the slurry comprises between about 400 ppm to about 700 ppm citric acid.

7. The talc slurry of claim 1, wherein the magnesium sulfate heptahydrate is added in the amount of between about 100 ppm to about 1500 ppm.

8. The talc slurry of claim 1, wherein the magnesium sulfate heptahydrate is added in the amount of between about 700 ppm to about 1300 ppm.

9. The talc slurry of claim 1, wherein the magnesium sulfate heptahydrate is added in the amount of about 700 ppm.

10. The talc slurry of claim 1, wherein the slurry has a specific gravity of between about 1.5 and about 1.8.

11. The talc slurry of claim 1, wherein said talc slurry has a viscosity of less than about 500 centipoise after agitation.

12. The talc slurry of claim 11, wherein said talc slurry has a viscosity of at least about 40,000 centipoise after storage for greater than about 4 hours.

13. The talc slurry of claim 1, wherein said talc has a mass median $d_{50}$ of from about 1.2 µm to about 3.5 µm.

14. The method of claim 2, wherein the solvent has a pH between about 10.2 and about 11.8.

15. The method of claim 2, wherein the phyllosilicate mineral is selected from the group consisting of kaolinites, talc, chlorites, pyrophyllites, montmorillonites, smectites and vermiculites.

16. The method of claim 2, wherein the phyllosilicate mineral is talc.

17. The method of claim 2, wherein the phyllosilicate mineral comprises between about 50% and about 80% of the slurry by weight.

18. The method of claim 2, wherein the phyllosilicate mineral comprises at least about 60% of the slurry by weight.

19. The method of claim 2, wherein the slurry comprises between about 50 ppm to about 850 ppm citric acid.

20. The method of claim 2, wherein the slurry comprises between about 400 ppm to about 700 ppm citric acid.

21. The method of claim 2, wherein said phyllosilicate mineral has a mass median $d_{50}$ of from about 1.2 µm to about 3.5 µm.

22. The method of claim 2, wherein the multivalent ions comprise cations selected from the group consisting of magnesium ions and aluminum ions.

23. The method of claim 2, wherein the multivalent ions comprise anions selected from the group consisting of sulfate ions and citrate ions.

24. The method of claim 3, wherein the magnesium sulfate heptahydrate is added in the amount of between about 100 ppm to about 1500 ppm.

25. The method of claim 3, wherein the magnesium sulfate heptahydrate is added in the amount of between about 700 ppm to about 1300 ppm.

26. The method of claim 3, wherein the magnesium sulfate heptahydrate is added in the amount of about 700 ppm.

27. A method of making a phyllosilicate mineral mineral slurry, comprising:
adding a phyllosilicate mineral to a solvent to produce a substantially homogeneous high solids slurry;
adding citric acid to the slurry; and,
adding magnesium sulfate heptahydrate to the slurry comprising the chelating agent to produce a stable phyllosilicate mineral slurry, and wherein the magnesium sulfate heptahydrate is present in a stoichiometric amount greater than the stoichiometric amount of citric acid.

28. The method of claim 3, wherein the solvent has a pH between about 10.2 and about 11.8.

29. The method of claim 3, wherein the phyllosilicate mineral is selected from the group consisting of kaolinites, talc, chlorites, pyrophyllites, montmorillonites, smectites and vermiculites.

30. The method of claim 3, wherein the phyllosilicate mineral is talc.

31. The method of claim 3, wherein the phyllosilicate mineral comprises between about 50% and about 80% of the slurry by weight.

32. The method of claim 3, wherein the phyllosilicate mineral comprises at least about 60% of the slurry by weight.

33. The method of claim 3, wherein the chelating agent is selected from the group consisting of sodium polyacrylate, sodium maleate, citric acid, sodium citrate, sodium silicate, EDTA, DTPA and mixtures thereof.

34. The method of claim 27, wherein the solvent has a pH between about 10.2 and about 11.8.

35. The method of claim 27, wherein the phyllosilicate mineral is selected from the group consisting of kaolinites, talc, chlorites, pyrophyllites, montmorillonites, smectites and vermiculites.

36. The method of claim 27, wherein the phyllosilicate mineral is talc.

37. The method of claim 27, wherein the phyllosilicate mineral comprises between about 50% and about 80% of the slurry by weight.

38. The method of claim 27, wherein the phyllosilicate mineral comprises at least about 60% of the slurry by weight.

* * * * *